July 7, 1970 R. L. BYRUM Plant Pat. 2,978
ROSE PLANT
Filed Aug. 16, 1968
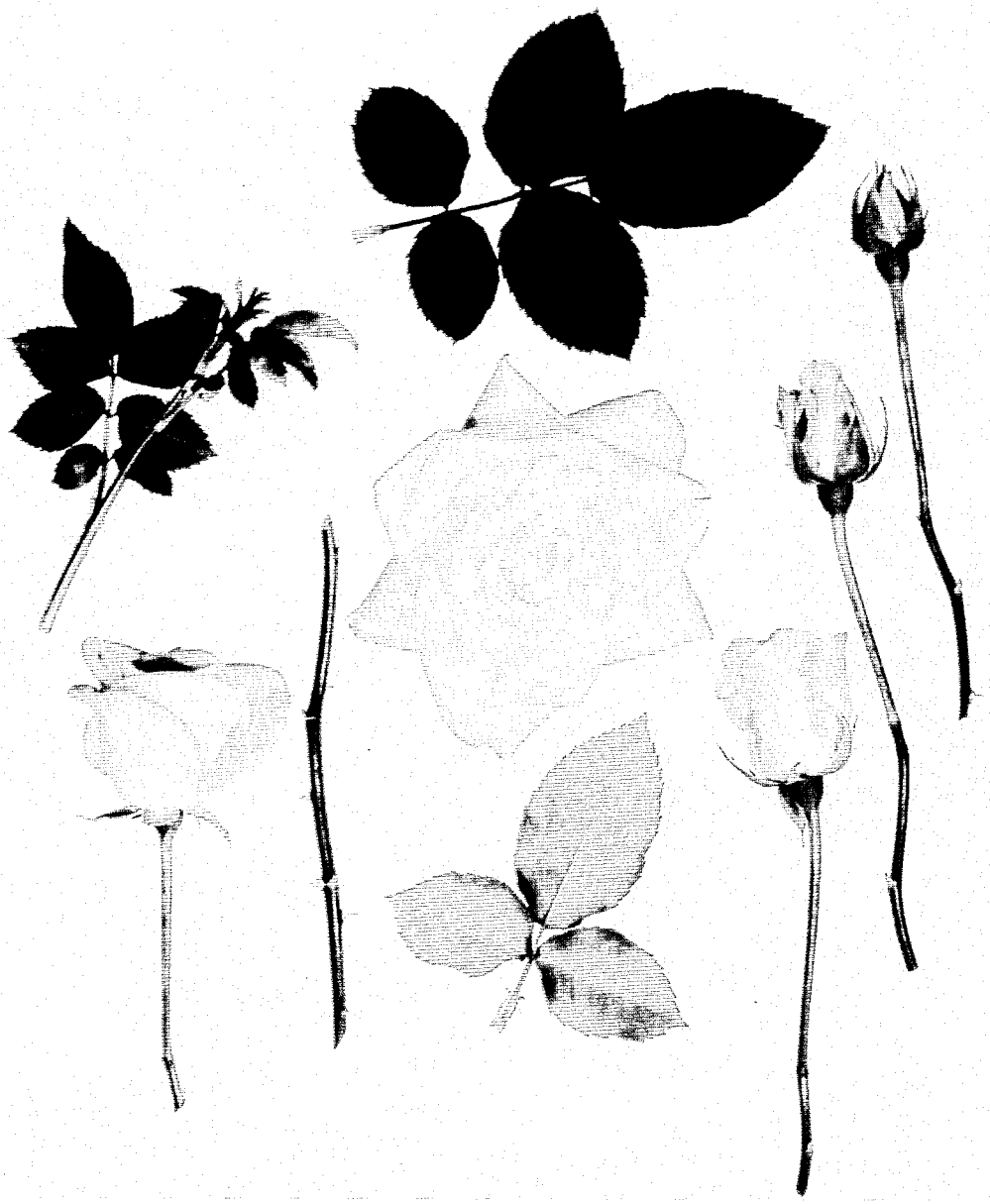
Inventor.
Roy L. Byrum
By: Robb & Robb
Attorneys.

United States Patent Office

Plant Pat. 2,978
Patented July 7, 1970

2,978
ROSE PLANT

Roy L. Byrum, Richmond, Ind., assignor to Joseph H. Hill Company, Richmond, Ind., a corporation of Indiana Filed Aug. 16, 1968, Ser. No. 753,324
Int. Cl. A01h 5/00
U.S. Cl. Plt.—11 1 Claim The present invention relates to a new and distinct variety of rose plant of the hybrid-tea class, which was originated by me by crossing the rose variety known as "Rumba" (Plant Pat. No. 1,919) with the rose variety known as "Golden Garnette" (Plant Pat. No. 1,898), the former being the seed parent and the latter being the pollen parent.

The primary objective of this breeding was to produce a new and improved rose variety having the keeping qualities of the parent variety "Rumba," but which has greater flower productivity than this parent variety, with the flowers of the new variety being of larger size. This objective was fully achieved, along with other desirable improvements, as evidenced by the following unique combination of characteristics which are outstanding in the new variety and which distinguish it from its parents, as well as from all other rose varieties of which I am aware:

(1) A free and vigorous plant habit;
(2) Long flower stems;
(3) A medium-large flower size;
(4) A distinctive, attractive and iridescent bi-color flower effect of pink and yellow colors; and
(5) Good keeping qualities.

In comparison with its seed parent, my new variety is a definite improvement thereover by virtue of its better greenhouse flower production, bears larger blooms, and has longer flower stems.

As compared with its pollen parent, the new variety produces larger blooms, and the blooms are borne on longer stems.

Asexual reproduction of my new variety by grafting, as performed at Richmond, Ind., and also by budding, as performed in California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)), and Koster's Color Guide (hereinafter abbreviated as (K)), except where general color terms of ordinary dictionary significance are obvious:

Type: Bush; seedling; for greenhouse production of cut flowers.
Class: Hybrid-tea.
Breeding: Seedling.
*Seed parent.*—"Rumba."
*Pollen parent.*—"Golden Garnette."
Propagation: Holds its distinguishing characteristics through succeeding propagations by both grafting and budding.

FLOWER

Locality where grown and observed: Richmond, Ind.
Flowers borne: Singly to stem; on stems of medium length and medium strength.
Quantity of bloom: Abundant, in greenhouse.
Continuity: Continuous, in greenhouse.

Fragrance (in greenhouse): Moderate. Nature—tea.
Bud:
*Peduncle.*—Strong; erect; medium length; medium diameter. Bark—almost smooth; color—Fern Green, Plate 0862 (W). Thorns—none. Prickles—none. Hairs—few; color—a very light shade of Lilac, Plate 48 (K).
*Before calyx breaks.*—Size—medium small. Form—short pointed; with a conspicuous neck; with foliaceous appendages on the surface of the bud; with slender foliaceous parts extending beyond the tip of the bud equal to ¼ or more of its length. Color—Chrysanthemum Crimson, Plate 824/3 (W).
*As calyx breaks.*—Color—Spinel Red, Plate 0023 (W).
*As first petal opens.*—Size—medium large. Form—pointed; ovoid. Color: outside—Edged Rose Opal, Plate 022 (W), gradually changing through Rose Opal, Plate 022/3 (W), with base of Empire Yellow, Plate 603/2 (W); inside—Rose Opal, Plate 022 (W), with base of Empire Yellow, Plate 603/1 (W).
*Opening.*—Opens well in greenhouse; no unusual characteristics observed.
Bloom:
*Size (when fully open).*—Medium large; from 3 inches to 4 inches in diameter.
*Petalage.*—Double; from 30 to 35 petals; arranged regularly.
*Form.*—Full and high-centered at first, remaining high-centered; petals at first being tightly rolled outward, but later becoming loosely rolled outward at maturity.
Petals:
*Texture.*—Moderately thick.
*Appearance.*—Inside—satiny. Outside—satiny.
*Shape.*—Outer petals—obvate, with apex mucronate. Intermediate petals—obvate, with apex mucronate. Inner petals—obvate, with apex mucronate.

This description of a newly opened flower was made from a rose grown in a greenhouse during the month of June at Richmond, Ind.:

*Color.*—Outer petals: outside surface—French Rose, Plate 520/3 (W), with base Empire Yellow, Plate 603/2 (W) fading into Empire Yellow, Plate 603/3 (W); inside surface—Rose Madder, Plate 23/2 (W), overlaid with Rose Madder, Plate 23/1 (W), with base Mimosa Yellow, Plate 602/2 (W) fading into Mimosa Yellow, Plate 602/3 (W). Intermediate petals: outside surface—Venetian Pink, Plate 420/3 (W), with base Empire Yellow, Plate 603/2 (W) fading into Empire Yellow, Plate 603/3 (W); inside surface—Camellia Rose, Plate 622/2 (W), overlaid with Camellia Rose, Plate 622/1 (W), with base Empire Yellow, Plate 603/1 (W) fading into Empire Yellow, Plate 603/2 (W). Inner petals: outside surface—Venetian Pink, Plate 420/3 (W), with base Empire Yellow, Plate 603/2 (W) fading into Empire Yellow, Plate 603/3 (W); inside surface—Camellia Rose, Plate 622/2 (W), overlaid with Camellia Rose, Plate 622/1 (W), with base Empire Yellow, Plate 603/1 (W) fading into Empire Yellow, Plate 603/2 (W). Inner petals: outside surface—Venetian Pink, Plate 420/3 (W), with base Empire Yellow, Plate 603/2 (W) fading into Empire Yellow, Plate 603/3 (W); inside surface—Camellia Rose, Plate 622/2 (W), overlaid with Camellia Rose, Plate 622/1 (W), with base Empire Yellow, Plate 603/1 (W) fading into Empire Yellow, Plate 603/2 (W).

This description was made from a rose that was open for three days in a greenhouse during the month of January at Richmond, Ind.:

*Color.*—Outer petals: outside surface—Rose Pink, Plate 427/3 (W), with base Canary Yellow, Plate 2/3 (W); inside surface—Rose Madder, Plate 23/1 (W), with base Canary Yellow, Plate 2/3 (W). Intermediate petals: outside surface—Rose Pink, Plate 427/3 (W), with base Canary Yellow, Plate 2/3 (W); inside surface—Rose Madder, Plate 23/2 (W), with base Canary Yellow, Plate 2/3 (W). Inner petals: outside surface—Rose Pink, Plate 427/3 (W), with base Canary Yellow, Plate 2/3 (W); inside surface—Neyron Rose, Plate 623/1 (W), with base Canary Yellow, Plate 2/3 (W).

*General color effect.*—Newly opened flower—bi-color effect of Nasturtium Orange, Plate 610/3 (W), encircled by Camellia Rose, Plate 622/2 (W). Three-days open—Neyron Rose, Plate 623/1 (W).

*Behavior.*—Persist, in greenhouse.

*Flower longevity.*—Cut roses grown in greenhouse and kept at living-room temperatures—5 or 6 days in May.

PLANT

Foliage:

*Leaves.*—Compound of 5 and 7 leaflets; abundant; medium large size; moderately heavy; leathery.

*Leaflets.*—Shape — ovoid. Apex — acute. Base — round. Margin—simply serrate.

*Color.*—Mature: upper surface—near Spinach Green, Plate 0960 (W); under surface—near Apple Green, Plate 77(K). Young: upper surface—Scheele's Green, Plate 860/2 (W), edged with Oxblood Red, Plate 00823/2 (W); under surface—Pod Green, Plate 061/1 (W), lightly washed with Oxblood Red, Plate 00823/3 (W).

*Rachis (the supporting stem of the compound leaf).*—Medium light. Upper side—grooved. Under side—prickly.

*Stipules.*—Short; narrow; with moderately short points turning out at an angle of less than 45°.

Growth (in a greenhouse):

*Habit.*—Bush; upright; much branched.

*Growth.*—Free; vigorous.

*Canes.*—Medium diameter.

*Main stems.*—Color—Spinach Green, Plate 0960/2 (W). Thorns—several; medium length; hooked downward; with short, narrow base; color—Maroon, Plate 97 (K). Prickles—none. Hairs—none.

*Branches.*—Color—Scheele's Green, Plate 860 (W). Thorns—several; medium length; hooked downward; with short, narrow base; color—from Lilac, Plate 48 (K) to Lilac Rose, Plate 49 (K). Prickles—none. Hairs—none.

*New shoots.*—Color—Scheele's Green, Plate 860/3 (W). Thorns—several; medium length; hooked downward; with short, narrow base; color—Sap Green, Plate 62/3 (W). Prickles—none. Hairs—none.

REPRODUCTIVE ORGANS

Stamens: Medium number; arranged regularly about pistils.

Filaments: Medium length; most with anthers. Color—Spanish Orange, Plate 010/3 (W).

Anthers: Medium size; all open at once. Color—Spanish Orange, Plate 010/3 (W), edged with darker shades of Spanish Orange, Plates 010/2 (W) and 010/1 (W).

Pollen: Abundant. Color—Orange Buff, Plate 507/3 (W).

Pistils: Medium number.

Styles: Even; short; moderately thin; bunched. Color—Primrose Yellow, Plate 601/3 (W), with upper tip Carmine, Plate 21/1 (W).

Stigma: Color—Maize Yellow, Plate 607/3 (W).

Ovaries: Some protruding from calyx.

Sepals: Permanent; medium length; straight; spear-shaped. Color: inside—Scheele's Green, Plate 860/1 (W), overlaid with white fuzz; outside—Scheele's Green, Plate 860/1 (W).

Seeds: Many; medium large size.

I claim:

1. A new and distinct variety of rose plant of the hybrid-tea class, substantially as herein shown and described, characterized particularly as to novelty by the unique combination of a free and vigorous plant habit, long flower stems, a medium-large flower size, a distinctive, attractive and iridescent bi-color flower effect of pink and yellow colors, and good keeping qualities.

No references cited.

ROBERT E. BAGWILL, Primary Examiner